United States Patent
Vaes et al.

(10) Patent No.: US 10,828,860 B2
(45) Date of Patent: Nov. 10, 2020

(54) USE OF POLYETHYLENE MATERIALS IN THE PRODUCTION OF STERILISABLE LIQUID CONTAINERS

(71) Applicant: SABIC Global Technologies B.V., Bergen op Zoom (NL)

(72) Inventors: Marnik Vaes, Belgium (DE); Bernardus Aldegonda Josephus Raven, Oirsbeek (NL)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 477 days.

(21) Appl. No.: 15/736,591

(22) PCT Filed: Jun. 17, 2016

(86) PCT No.: PCT/EP2016/064081
§ 371 (c)(1),
(2) Date: Dec. 14, 2017

(87) PCT Pub. No.: WO2016/203016
PCT Pub. Date: Dec. 22, 2016

(65) Prior Publication Data
US 2018/0179307 A1 Jun. 28, 2018

(30) Foreign Application Priority Data
Jun. 18, 2015 (EP) .................... 15172647

(51) Int. Cl.
| | |
|---|---|
| *B32B 1/02* | (2006.01) |
| *B65D 1/02* | (2006.01) |
| *B29C 49/00* | (2006.01) |
| *B29C 49/42* | (2006.01) |
| *C08F 210/02* | (2006.01) |
| *B32B 1/08* | (2006.01) |
| *C08F 110/02* | (2006.01) |
| *A61J 1/14* | (2006.01) |
| *A61J 1/10* | (2006.01) |
| *A61L 2/04* | (2006.01) |
| *B29C 49/02* | (2006.01) |
| *B29L 31/00* | (2006.01) |
| *B29C 49/04* | (2006.01) |
| *B29C 49/64* | (2006.01) |

(52) U.S. Cl.
CPC ............ *B32B 1/02* (2013.01); *A61J 1/10* (2013.01); *A61J 1/1468* (2015.05); *A61L 2/04* (2013.01); *B29C 49/0005* (2013.01); *B29C 49/02* (2013.01); *B29C 49/4273* (2013.01); *B32B 1/08* (2013.01); *B65D 1/0207* (2013.01); *B65D 1/0261* (2013.01); *C08F 110/02* (2013.01); *C08F 210/02* (2013.01); *A61L 2202/23* (2013.01); *B29C 49/04* (2013.01); *B29C 49/64* (2013.01); *B29K 2023/06* (2013.01); *B29L 2031/7128* (2013.01); *B29L 2031/7148* (2013.01); *B29L 2031/7158* (2013.01); *C08F 2500/12* (2013.01)

(58) Field of Classification Search
CPC . B32B 1/02; B32B 1/08; C08F 210/02; C08F 210/04; C08F 210/06; C08F 210/08; C08F 210/10; B65D 1/0207; B65D 1/0261
See application file for complete search history.

(56) References Cited

U.S. PATENT DOCUMENTS

| | | | |
|---|---|---|---|
| 2011/0120058 A1 | 5/2011 | Radermacher | |
| 2012/0220738 A1* | 8/2012 | Mannebach | C08F 110/02 526/64 |

FOREIGN PATENT DOCUMENTS

| | | |
|---|---|---|
| EP | 0601631 A1 | 6/1994 |
| EP | 2239283 A1 | 10/2010 |
| WO | 2005065818 A1 | 7/2005 |

OTHER PUBLICATIONS

International Search Report for International Application No. PCT/EP2016/004081, International Filing Date Jun. 17, 2016, dated Aug. 5, 2016, 6 pages.
Written Opinion for International Application No. PCT/EP2016/004081, International Filing Date Jun. 17, 2016, dated Aug. 5, 2016, 5 pages.

* cited by examiner

*Primary Examiner* — Walter Aughenbaugh
(74) *Attorney, Agent, or Firm* — Cantor Colburn LLP

(57) ABSTRACT

The present invention relates to the use of a polyethylene material in liquid containers that are sterilisable at a temperature of ≥100° C. during a period of >15 minutes, wherein the polyethylene material has a density >928 kg/m³ as determined according to ISO 1183-1, method A, and a melt mass flow rate of ≥0.50 and 51.00 g/10 min as determined according to ISO 1133-1 at a temperature of 190° C. and a load of 2.16 kg; wherein the polyethylene material produced in a high-pressure free-radical polymerisation process at a pressure of ≥1600 bar.

15 Claims, No Drawings

USE OF POLYETHYLENE MATERIALS IN THE PRODUCTION OF STERILISABLE LIQUID CONTAINERS

CROSS REFERENCE TO RELATED APPLICATIONS

This application is a 371 of International Application No. PCT/EP2016/064081, filed Jun. 17, 2016, which claims priority to European Application No. 15172647.8, filed Jun. 18, 2015, both of which are incorporated herein by reference in their entirety.

The present invention relates to the use of a polyethylene material in the production of liquid containers sterilisable at ≥100° C.

In order for liquid containers for medical applications to be suitable for a safe use in treatment of patients, as humans and animals, such containers are often used only once and subjected to a sterilisation treatment. Polymer materials and especially polyethylene are thereby easy to process in a so called blow-fill-seal process, where the liquid container is formed especially for example by blow moulding, filled with a liquid and sealed. Polyethylene can further be recycled, so that it is often used for such kind of application. The sterilisation treatment is thereby directed at reducing the quantity of micro-organisms present in or on an object in such way as to reduce any associated risk to the health of the patient that undergoes a treatment involving such containers.

Liquid containers for medical applications that may undergo sterilisation treatments are for example described in EP601631A1. EP601631A1 describes containers made from polyethylene compositions comprising 20-50 wt % linear low-density polyethylene having a density of 915-935 kg/m$^3$ and 50-80 wt % of a linear low-density polyethylene having a density of 920-965 kg/m$^3$. Such containers are subjected to sterilisation at 110° C. No indication is presented as to the period of sterilisation. A disadvantage of such containers is that they comprise linear low-density polyethylene materials which, by nature of their production process, contain residues originating from catalysts. Such residues may for example include tetrahydrofuran, chromium, zirconium and/or hafnium. Because of the presence of such restudies, these materials are not suitable for certain medical applications.

On the other hand, US20110120058A1 describes the use of linear low-density polyethylenes prepared using a zirconium-metallocene catalyst, in which the linear low-density polyethylene has a density of 935 kg/m$^3$, from which pouches are made that are subjected to sterilisation at 119° C. for 15 minutes. Also for these containers, a disadvantage is that they comprise linear low-density polyethylene materials which again contains residues from the catalyst.

In view of increasingly stringent expectations, requirements and regulations relating to materials to be used in medical applications to safeguard patients' health and safety, such residues become more and more undesirable.

Therefore, it is clear that there is an ongoing need to find new materials suitable for liquid containers sterilisable at high temperatures and fulfilling the demanding expectations for such materials.

This has now been achieved according to the present invention by the use of a polyethylene material for liquid containers sterilisable at a temperature of ≥100° C. during a period of ≥15 minutes,
wherein the polyethylene material has a density ≥928 kg/m$^3$ as determined according to ISO 1183-1 (2012), method A, and a melt mass flow rate of ≥0.30 and ≤1.00 g/10 min as determined according to ISO 1133-1 (2011) at a temperature of 190° C. and a load of 2.16 kg;
wherein the polyethylene material produced in a high-pressure free-radical polymerisation process at a pressure of ≥1600 bar.

The use according to the present invention is preferably for example for disposable liquid containers, that may thus be used only once. The use according to the present invention moreover is preferably for example for aseptic packaging.

The density of the polyethylene material used according to the invention as determined according to ISO 1183-1 (2012), method A may for example be ≤950 kg/m$^3$, alternatively ≤940 kg/m$^3$, alternatively ≤935 kg/m$^3$, alternatively ≤930 kg/m$^3$. The density of the polyethylene material used according to the invention as determined according to ISO 1183-1 (2012), method A may for example be ≥928 kg/m$^3$. Such density may for example contribute to a good shape stability during sterilisation. Shape stability can be understood to be the retention of the original shape of liquid container or filled liquid container during sterilisation. A liquid container that has good shape stability may for example not show thermal deformation or durable thermal deformation during sterilisation. A liquid container that has good shape stability during sterilisation may thus for example preferably not demonstrate changes in shape, especially durable changes in shape, such as for example the formation of bumps, ripples, dents and/or bulges and/or sagging and/or changes of volume. Durable may thereby mean that persists and/or remains visible after sterilisation. A liquid container that has good shape stability may for example preferably also not leak during sterilisation. A good shape stability during sterilisation thereby becomes increasingly important not only for aesthetic reasons but also because it strongly fosters the medical personnel's confidence and the ability to subject the liquid container to proper sterilisation as well as well as the trust in a quality treatment.

The melt mass flow rate of the polyethylene material used according to the invention as determined according to ISO 1133-1 (2011) at a temperature of 190° C. and a load of 2.16 kg may for example be ≤1.00 g/10 min, alternatively ≤0.90 g/10 min, alternatively ≤0.80 g/10 min, alternatively ≤0.70 g/10 min, alternatively ≤0.60 g/10 min. The melt mass flow rate of the polyethylene material as determined according to ISO 1133-1 (2011) at a temperature of 190° C. and a load of 2.16 kg may for example be ≥0.30 g/10 min, alternatively ≥0.35 g/10 min, alternatively ≥0.40 g/10 min, alternatively ≥0.45 g/10 min, alternatively ≥0.50 g/10 min. The melt mass flow rate of the polyethylene material as determined according to ISO 1133-1 (2011) at a temperature of 190° C. and a load of 2.16 kg may for example be ≥0.30 and ≤1.00 g/10 min, alternatively ≥0.40 and ≤0.80 g/10min, alternatively ≥0.50 and ≤0.60 g/10 min. Such melt mass flow rate may for example result in a material having good processability in blow-fill-seal production processes. Such melt mass flow rate may for example contribute to a good processability and/or a good melt stability in the parison blow moulding stage in the blow-fill-seal production process. Furthermore, it may also contribute to a good shape stability during sterilisation.

In the context of the present invention, liquid containers may for example be bottles, vials, ampoules, tubes, bags or pouches. For example, the liquid containers may be flexible containers, such as flexible intravenous bag or flexible intravenous bottles, preferably a (pre-) filled with a liquid. The liquid container can thereby for example contain for example liquids, solutions and/or suspensions of medical materials used for medical treatment of patients, including for example intravenous treatments. The liquid containers may furthermore for example have a volume of ≥0.100 l, alternatively ≥0.200 l, alternatively ≥0.400 l, alternatively ≥0.500 l. Such liquid containers may for example have a volume of ≤2.000 l, alternatively ≤1.500 l, alternatively ≤1.000 l, alternatively ≤0.750 l. For example, such liquid containers may have a volume of ≥0.100 l ands ≤1.000 l, alternatively ≥0.200 l and ≤0.750 l.

Liquid containers according to the present invention may for example be sterilisable via a heat treatment. For example, this heat treatment may especially take place in the presence of steam and/or under pressure, especially in an autoclave. For example, such pressure may be between 1 bar and 3 bar, preferably between 2 bar and 3 bar, further preferred ≤10 bar. The duration of the sterilisation process may for example be ≥15 min, alternatively ≥30 min, alternatively ≥45 min, alternatively ≥60 min, alternatively ≥75 min. The liquid containers according to the present invention may for example be sterilisable at temperatures of ≥100° C., alternatively ≥105° C., alternatively ≥110° C., preferably between 110° C. and 115° C., even more preferred at 110° C.

At such high temperatures and especially for examples for duration of ≥15 min shape stability becomes increasingly difficult to maintain. The materials used according to the present invention have thereby surprisingly show very good shape stability even for sterilisation at relatively high temperatures and/or for long durations.

In an embodiment, a liquid container may be for example pre-filled. In the context of the present invention, pre-filled is to be understood to be filled upon or right after production of the liquid container and/or prior to being subjected to a sterilisation process. A pre-filled liquid container may for example be produced by filling the liquid container as part of its production process or right thereafter, especially for example in a so-called 'blow-fill-seal'-process (BFS-process). In such a BFS-process liquid containers may be produced by an extrusion blow moulding process, in which directly upon moulding of the liquid container or right thereafter, it is filled with a liquid material and sealed. Alternatively, liquid containers may be also produced by extrusion blow moulding and filled at a later stage.

The polyethylene material used according to the present invention may for example be a polyethylene material comprising ≥90.0 mol-%, alternatively ≥95.0 mol-%, alternatively ≥98.0 mol-%, alternatively ≥99.0 mol-%, alternatively ≥99.9 mol-%, of structural units in the polymer chains deriving from ethylene monomers. It may also preferably for example not comprise catalyst/metal residues, such as especially metallocene residues, and/or any LLDPE.

The polyethylene material used according to the present invention may preferably for example be produced in a high-pressure free-radical polymerisation process. The polyethylene material may for example be produced in a tubular reactor. The polyethylene may for example be produced in a polymerisation process operated at a pressure of ≥1600 bar, alternatively ≥1800 bar, alternatively ≥2000 bar, alternatively ≥2200 bar, alternatively ≥2400 bar. The polyethylene material may for example be produced in the presence of a free-radical initiator and/or without using a catalyst and/or without using any metal containing compound. The production method thereby for example influences the structure, crystallinity and/or molecular weight distribution of the polyethylene material and thereby contributes both to a good processability and a very good shape stability during sterilisation.

In the production of polyethylenes via free-radical high-pressure polymerisation processes, catalysts comprising tetrahydrofuran, chromium, hafnium and/or zirconium are not used. Accordingly, no residues of such deriving from catalysts used in the polymerisation process remain in polyethylenes produced via such process.

The use according to the present invention may be for liquid containers that can for example comprise multiple layers. Alternatively, use according to the present invention may be for liquid containers that preferably consist of a single layer.

The use according to the present invention may be for liquid container produced via a process comprising the steps of:
 a) providing a melt comprising the polyethylene material;
 b) shaping the molten material into a tubular parison having a shape comprising an opening;
 c) positioning said parison in a mould having the desired shape of said liquid container, in which the parison is held at such temperature that the parison may be shaped into the shape of the liquid container by pressurising the inside of the parison with a pressurised gas to form the liquid container having at least one opening;
 d) optionally cooling the liquid container,
 e) filling the liquid container with a liquid product for for medical treatment of patients; and
 f) sealing the at least one opening of the liquid container wherein the liquid container may be subjected to a sterilisation treatment at a temperature of ≥100° C. during a period of ≥15 minutes.

Said melt may thereby be provided by subjecting the polyethylene material to a melt extrusion process. Said parison may be produced for example by feeding the molten material from the melt extrusion process into a mold having the shape of the parison. The pressurised gas may be a sterilized and/or medical grade gas.

The use according to the present invention may be for liquid container with a wall thickness of ≤200 μm, alternatively ≤150 μm, alternatively ≤100 μm. For example, such layer may have a thickness of ≥20 μm, alternatively ≥50 μm. For example, such layer may have a thickness of ≥20 and ≤150 μm, alternatively ≥50 and ≥100 μm.

The use according to the present invention may be for liquid container produced via a process in which the sealing step f) is performed by
 heating the material of the liquid container in the area of the opening to a temperature above the softening temperature to provide an area of softened material;
 sealing of the opening by bringing the softened material of the liquid container into such contact that the opening is closed; and
 cooling of the softened material to a temperature below the softening temperature.

The invention will now be illustrated by the following non-limiting examples.

Liquid containers were prepared in the same way for example I and II on a Rommelag Bottlepack 321 Blow-Fill-Seal machine. The only difference thus being in the material used.

Example I was performed according to the invention; example II was performed using a polyethylene material for comparative purposes.

|  | Example | |
|---|---|---|
|  | I | II (comparative) |
| Polyethylene material | PE-A | PE-B |
| Density | 928 kg/m$^3$ | 927 kg/m$^3$ |
| Melt mass flow rate | 0.55 g/10 min | 0.30 g/10 min |
| Shape stability during sterilisation | Good | Poor; bumps/rippling occurring |

PE-A was a polyethylene of the grade SABIC® LDPE PCG06 obtainable from SABIC, produced in a tubular high-pressure free-radical polymerisation process at a pressure of 2800 bar; PE-B was a polyethylene of the grade PE3020D obtainable from LyondellBasell.

The density was determined in accordance with ISO 1183-1 (2012), relating to methods for the determination of density of non-cellular plastics, using method A.

The melt mass flow rate was determined in accordance with ISO 1133-1 (2011), relating to the determination of the melt mass-flow rate and the melt volume-flow rate of thermoplastics, at a temperature of 190° C. and a load of 2.16 kg.

Shape stability on sterilisation is determined by subjecting liquid containers obtained from examples I and II to a sterilisation treatment with steam in an autoclave at a temperature of 106° C. for 85 minutes. After that sterilisation treatment shape stability during sterilisation has been assessed visually.

The presented examples show that the use of a polyethylene material having a density of ≥928 kg/m$^3$ as determined according to ISO 1183-1 (2012), method A, and a melt mass flow rate of ≥0.30 and ≤1.00 g/10 min as determined according to ISO 1133-1 (2011) at a temperature of 190° C. and a load of 2.16 kg, produced in a high-pressure free-radical polymerisation process at a pressure of ≥1600 bar for the production of liquid containers sterilisable at ≥100° C. can surprisingly lead to an significantly increased shape stability during sterilisation compared to the use of an industry standard material, frequently used for such application and having otherwise very similar properties.

The invention claimed is:

1. A liquid container, comprising:
   a polyethylene material having a density ≥928 and ≤930 kg/m$^3$ as determined according to ISO 1183-1 (2012), method A, and a melt mass flow rate of ≥0.50 and ≤0.7 g/10 min as determined according to ISO 1133-1 (2011) at a temperature of 190° C. and a load of 2.16 kg;
   wherein the polyethylene material was produced in a high-pressure free-radical polymerisation process at a pressure of ≥1600 bar;
   the liquid container has a wall thickness of ≥1600 bar;
   the liquid container is sterilisable at a temperature of ≥100° C. during a period of ≥15 minutes.

2. The liquid container of claim 1, wherein the liquid container is a bottle or an intravenous bag.

3. The liquid container of claim 2, wherein the liquid container is a sealed container containing a liquid material.

4. The liquid container of claim 1, wherein the liquid container is sterilisable at a temperature of ≥105° C. or of ≥110° C.

5. The liquid container of claim 1, wherein the liquid containers is sterilisable during a period of ≥60 minutes.

6. The liquid container of claim 1, wherein the liquid container is produced with a BFS-process.

7. The liquid container of claim 1, wherein the liquid container consists of a single layer.

8. The liquid container of claim 1, wherein the liquid container is disposable.

9. The liquid container of claim 1, wherein the liquid container is produced via a process comprising the steps of:
   a) providing a melt comprising the polyethylene material;
   b) shaping the molten material into a tubular parison having a shape comprising an opening;
   c) positioning said parison in a mould having the desired shape of said liquid container, in which the parison is held at such temperature that the parison may be shaped into the shape of the liquid container by pressurising the inside of the parison with a pressurised gas to form the liquid container having at least one opening;
   d) filling the liquid container with a product for intravenous treatment; and
   e) sealing the at least one opening of the liquid container.

10. The liquid container according to claim 9 wherein the liquid container was produced via a process in which the sealing step e) is performed by
   heating the material of the liquid container in the area of the opening to a temperature above the softening temperature to provide an area of softened material;
   sealing of the opening by bringing the softened material of the liquid container into such contact that the opening is closed; and
   cooling of the softened material to a temperature below the softening temperature.

11. The liquid container of claim 1, wherein the polyethylene material is made in a tubular reactor.

12. The liquid container of claim 1, wherein the liquid container has a wall thickness of ≥20 μm and ≤150 μm.

13. The liquid container of claim 1, wherein the polyethylene material is produced in a high-pressure free-radical polymerisation process at a pressure of ≥2400 bar.

14. The liquid container of claim 1, wherein the liquid container is sterilisable at a temperature of ≥105° C. during a period of ≥60 minutes.

15. A liquid container, comprising:
   a polyethylene material having a density ≥928 and ≤930 kg/m$^3$ as determined according to ISO 1183-1 (2012), method A, and a melt mass flow rate of ≥0.50 and ≤0.6 g/10 min as determined according to ISO 1133-1 (2011) at a temperature of 190° C. and a load of 2.16 kg;
   wherein the polyethylene material was produced in a high-pressure free-radical polymerisation process at a pressure of ≥2400 bar;
   the liquid container has a wall thickness of ≥20 μm and ≤150 μm; and
   the liquid container is sterilisable at a temperature of ≥105° C. during a period of ≤60 minutes.

\* \* \* \* \*